United States Patent
Kawagishi et al.

Patent Number: 5,668,174
Date of Patent: Sep. 16, 1997

[54] METHOD OF TREATING HYPERPARATHYROIDISM

[75] Inventors: Fumikazu Kawagishi, Kawachinagano; Keiko Yamada, Osaka; Hiroshi Iguchi, Katano, all of Japan

[73] Assignee: Kowa Tekuno Sachi Co., Ltd., Osaka, Japan

[21] Appl. No.: 666,527

[22] PCT Filed: Oct. 14, 1994

[86] PCT No.: PCT/JP94/01729

§ 371 Date: Jul. 1, 1996

§ 102(e) Date: Jul. 1, 1996

[87] PCT Pub. No.: WO95/17889

PCT Pub. Date: Jul. 6, 1995

[30] Foreign Application Priority Data

Dec. 29, 1993  [JP]  Japan ................................ 5-355269

[51] Int. Cl.$^6$ ................................................ A61K 31/20
[52] U.S. Cl. ................................................ 514/560
[58] Field of Search ................................ 514/549, 560

[56] References Cited

FOREIGN PATENT DOCUMENTS

| 61126022 | 11/1984 | Japan. |
| 62-096421 | 5/1987 | Japan. |
| 6040904 | 2/1994 | Japan. |
| 6157304 | 6/1994 | Japan. |
| 6157305 | 6/1994 | Japan. |

OTHER PUBLICATIONS

Avery's Drug Treatment, 3rd ed., T.M. Speight Ed. p. 556. 1987.

*Primary Examiner*—Raymond Henley, III
*Attorney, Agent, or Firm*—Knobbe, Martens, Olson & Bear, LLP.

[57] ABSTRACT

A very safe therapeutic composition having a sufficient curative effect on hyperparathyroidism of a patient subjected to artificial dialysis, which composition contains as the active ingredient at least one member selected from γ-linoleic acid, dihomo-γ-linolenic and derivatives thereof.

2 Claims, No Drawings

METHOD OF TREATING HYPERPARATHYROIDISM

This application is a 371 of PCT/JP94/01729 filed Oct. 14, 1994.

TECHNICAL FIELD

The present invention relates to a therapeutic composition for suppressing hypersecretion of parathyroid hormone due to hyperparathyroidism of patients subjected to artificial dialysis.

BACKGROUND ART

The recent development of hemodialytic therapy has now greatly reduced death caused directly by chronic renal failure. Suitable therapy for chronic and renal failure has made it possible to live for another 20 year or longer. Accordingly, it has become extremely important to improve the quality of life (hereinafter referred to as QOL) of patients (that is, to let patients live an ordinary life without being physically handicapped or socially isolated. Therefore, at present, it is desirable to take measures against the complications of chronic renal failure from which patients may suffer while living for a long period of time and also undertake suitable therapeutic means for ensuring the patients' early rehabilitation in society.

Chronic renal failure exhibits a decrease in the number of nephrons irrespective of the type of renal disorder. The extended decrease in the number of nephrons results in the loss of renal function, which necessitates artificial dialysis. Renal depression due to a decrease in the number of nephrons causes a decrease in serum Ca, a decrease in the production of active vitamin D, elevation of the serum Ca set-point at which the secretion of parathyroid hormone (hereinafter referred to as PTH) is set to be suppressed, a decrease in the number of parathyroid-activated vitamin D receptors, the metabolic disorder involving phosphorus, etc., causing hypersecretion of PTH that may be followed by secondary hyperparathyroidism.

PTH is indispensable for the regulation of the metabolism of calcium and phosphorus, while having a great influence on the stable maintenance of bone. Hypersecretion of PTH acts on bone, thereby causing fibrous osteitis. It is said that PTH is one of uremic substances which cause anemia, organic ulcers, central nervous neuropathy, itching, hyperlipemia, etc. and it is a significant factor in the presentation of the symptoms of renal osteodystrophy which is a severe complication for patients subjected to artificial dialysis. Many patients who have once suffered from the disorder of renal osteodystrophy are difficult to cure, and the disorder noticeably lowers with the QOL for patients subjected to artificial dialysis.

It is said that most patients with light renal failure suffer from secondary hyperparathyroidism. The frequency and the degree of the complication increase in patients who are subjected to artificial dialysis for a long period of time. Therefore, it is necessary to prevent the complication in the early stages of renal failure.

To cure secondary hyperparathyroidism, for example, activated vitamin D preparations are administered to patients with hypocalcemia or those with insufficiency of vitamin D production. However, such preparations involve harmful side effects in that they often cause hypercalcemia and ectopic calcification. Pulse therapy may be administered to patients resistant to activated vitamin D preparations. However, pulse therapy is problematic in that it may cause hypometabolic turnover osteitis, etc., in addition to the above-mentioned disadvantages. In order to lower the serum Ca set-point at which the secretion of PTH is set to be suppressed, activated vitamin D preparations and calcium preparations may be employed, which, however, are still problematic for the above reasons. On the other hand, aluminum hydroxide is a chemical that should not be administered to patients with hyperphosphatemia caused by the metabolic disorder of phosphorus, who are subjected to artificial dialysis. Therefore, in place of this, calcium carbonate or calcium acetate preparations are administered to them. However, because of poor phosphorus adsorbability, calcium preparations must be administered in large quantities, resulting in a high risk of hypercalcemia. Low-protein dietary cure may also be employed with the limitation of phosphorus. However, low-protein diets often bring about negative results of trophopathy and hypercatabolism. Surgical treatment of an enucleating parathyroid gland may be employed, which, however, brings about serious mental and physical strains on patients.

As mentioned hereinabove, the conventional therapeutic means for hyperparathyroidism are all problematic. In particular, for patients subjected to artificial dialysis for a long period of time, even the combinations of such means produce unsatisfactory therapeutic effects at present.

DISCLOSURE OF THE INVENTION

The present invention has been attained from the above-mentioned viewpoints, and its object is to provide a therapeutic composition for hyperparathyroidism of patients subjected to artificial dialysis, which composition exhibits a sufficient curative effect without having any negative influence such as harmful side effects and can produce good results with regard to QOL.

The present inventors have assiduously studied in order to attain the above-mentioned object and, as a result, have found that ω-6 unsaturated fatty acids can significantly depress the hypersecretion of PTH caused by the hyperparathyroidism of patients subjected to artificial dialysis. On the basis of this finding, we have achieved the present invention.

The present invention provides a therapeutic composition for hyperparathyroidism of a patient subjected to artificial dialysis, comprising one or more selected from γ-linolenic acid, dihomo-γ-linolenic acid and derivatives thereof.

The present invention is described in detail hereinunder.

ω-6 unsaturated fatty acids such as γ-linolenic acid, dihomo-γ-linolenic acid, etc. which are used in the present invention, are known as indispensable fatty acids, and it is known that these and their derivatives (hereinafter referred to as "γ-linolenic acid, etc.") have various physiological activities. However, it was entirely unknown that these are effective on hyperparathyroidism of patients subjected to artificial dialysis, which effect we have found for the first time.

γ-linolenic acid, etc. to be used in the present invention are fatty acids indispensable to human bodies, and these are safe to patients with a dietary cure such as those subjected to artificial dialysis and can administrated to them without anxiety.

γ-linolenic acid, etc. can be obtained from oils and fats which originate from mold of the genera Mucor, Mortierella, Rizopus, etc., plants such as evening primrose, borage, etc. and also algae such as Spirulina, etc. Extracts from these may be used directly or after having been purified. In addition, γ-linolenic acid, etc. can also be obtained by chemical synthesis, and commercially-available products can also be used.

Derivatives of the above-mentioned γ-linolenic acid and dihomo-γ-linolenic acid include esters.

The form of the therapeutic composition of the present invention for hyperparathyroidism of patients subjected to artificial dialysis is not specifically defined. For example, one selected from γ-linolenic acid, dihomo-γ-linolenic acid and derivatives thereof, or a mixture of two or more of these, or an extract to be obtained from oils and fats such as those of the above-mentioned mold, plants, etc. is mixed with one or more of ordinary, pharmaceutically-acceptable harmless vehicles, carriers, excipients, binders, preservatives, stabilizers, flavorings, etc., and formed into internal preparations such as tablets, granules, capsules, liquid preparations, etc.; suppositories; vaginal preparations; external preparations such as ointments, creams, lotions, etc.; and injections such as sterilized solutions, suspensions, etc. These can be formulated in accordance with known techniques.

For example, one or more of the above-mentioned γ-linolenic acid, etc. may be formulated with a binder such as gelatin, etc., a vehicle such as crystalline cellulose, etc., an excipient such as potato starch, sodium alginate, etc., a sweetener such as lactose, sucrose, etc., and made into powders, tablets, pills or granules. To prepare capsules, a mixture of γ-linolenic acid, etc. and other oils and fats is encapsulated into soft gelatin capsules, hard gelatin capsules, etc., in accordance with known methods. In addition, cyclodextrin clathrates comprising cyclodextrin and γ-linolenic acid, etc. can also be prepared by known methods. To prepare external preparations, vaseline, paraffin, oils and fats, lanolin, etc. are usable as a base.

The above-mentioned γ-linolenic acid, etc. can be combined with ω-3 unsaturated fatty acids such as α-linolenic acid, eicosapentaenoic acid, docosahexaenoic acid, etc., ω-5 unsaturated fatty acids such as myristoleic acid, etc., ω-7 unsaturated fatty acids such as palmitoleic acid, etc., ω-9 unsaturated fatty acids such as oleic acid, ercylic acid, etc.; and saturated fatty acids such as lauric acid, myristic acid, etc., in any desired proportions. In order to prevent the oxidation of γ-linolenic acid, etc., antioxidants such as vitamin E, ascorbyl palmitate, ascorbyl stearate, etc. may be added thereto.

The dose of γ-linolenic acid, dihomo-γ-linolenic acid or its derivative is not specifically defined. However, if too much of it is administered, the patient is apt to have loose bowels. The dose shall be suitably determined, depending on the age, the medical history and the condition of the patient as well as the type of the disorder, etc. To attain the intended effects for the treatment of hyperparathyroidism, the active ingredient may be administered thereto in an amount of from 50 to 600 mg/day, preferably from 100 to 450 mg/day.

BEST MODES FOR CARRYING OUT THE INVENTION

Examples of the present invention are described hereinunder.

PRODUCTION EXAMPLE 1

Capsules 235 parts by weight of oil or fat containing about 22% by weight of γ-linolenic acid was mixed with 65 parts by weight of vitamin E (TM-70G, produced by Tama Biochemical Co.) by an ordinary method and encapsulated in gelatin capsules (Football-type No. 5, produced by Fuji Capsule Co.) to produce capsules each containing γ-linolenic acid of 50 mg/capsule.

The oil or fat containing γ-linolenic acid used herein was extracted according to the method described in Japanese Patent Application Laid-Open No. 63-283589 (1988). Briefly, cultured cells of *Mucor circinelloides* HUT 1121 (FERM P-9359) were subjected to n-hexane extraction to obtain oil or fat containing γ-linolenic acid.

EXAMPLE

Evaluation of Therapeutic Composition of the Invention

The capsules prepared in the above-mentioned Production Example were administered to four patients subjected to artificial dialysis, who suffer from hyperparathyroidism and have medical histories of hemodialytic treatment shown in Table 1 below, at 7 capsules/day (4 capsules after breakfast and 3 capsules after the evening meal each day) which corresponds to 350 mg of γ-linolenic acid per day. The administration was started on the same day for the four patients. For patients Nos. 1 to 3, administration was continued for 3 months. Then, their data were measured with Allegro Intact PTH kits (produced by Nippon Mediphysics Co.) and are shown in Table 2. For patient No. 4, administration was continued for 3 months and thereafter 3 capsules/day (corresponding to 150 mg of γ-linolenic acid per day) were continuously administered after breakfast for 5 months further. Data were then measured with a PTH kit "Yamasa" (produced by Yamasa Shoyu Co.) and are shown in Table 3. The PTH data of the four patients were periodically measured. Their PTH data before and after the administration are shown below along with the months counted on the basis of the start of administration.

TABLE 1

Background of Patients

| Patient No. | Sex | Age | Medical History of Hemodialytic Treatment (at the start of the administration) |
|---|---|---|---|
| 1 | Female | 44 | 1 year and 6 months |
| 2 | Female | 64 | 1 year and 2 months |
| 3 | Female | 42 | 10 years and 11 months |
| 4 | Male | 46 | 2 years and 9 months |

TABLE 2

PTH Data (measured with Allegro Intact PTH kit - normal value: 11 to 54 pg/ml)

| Patient No. | 3 Months Before Administration | 3 Months Administration |
|---|---|---|
| 1 | 295 | 153 |
| 2 | 300 | 69 |
| 3 | 816 | 427 |

TABLE 3

PTH Data (measured with PTH Kit "Yamasa" - normal value: 160 to 520 pg/ml)

Patient No. 4

Before Administration

| 13 months before | 14,000 |
|---|---|
| 12 months before | 14,000 |

TABLE 3-continued

PTH Data (measured with PTH Kit "Yamasa" - normal value: 160 to 520 pg/ml)

Patient No. 4

| | |
|---|---|
| 10 months before | 17,000 |
| 7 months before | 17,000 |
| 4 months before | 19,000 |
| 1 months before | 22,000 |
| Administration | |
| 2 months after | 22,000 |
| 5 months after | 14,000 |
| 8 months after | 12,000 |

From the results in Table 2 and Table 3, it is evident that the PTH values of the four patients who are subjected to artificial dialysis and to whom the therapeutic composition for hyperparathyroidism of the present invention was administered all declined after administration. From these data, it is obvious that the composition of the present invention is efficacious against hyperparathyroidism. Before and after administration, no particular medical treatment was administered to the patients. No abnormal changes were found in their periodically measured clinical examination data. The safety of the composition of the present invention was thus confirmed.

INDUSTRIAL APPLICABILITY

The therapeutic composition of the present invention for hyperparathyroidism of patients who are subjected to artificial dialysis exhibits a marked suppressive effect on the hypersecretion of PTH caused by hyperparathyroidism, and is excellent in terms of safety.

What is claimed is:

1. A method for treating hyperparathyroidism of patients suffering from hyperparathyroidism associated with renal disorder, comprising administering to said patients at least one ω-6 unsaturated fatty acid composition selected from the group consisting of γ-linolenic acid, dihomo-γ-linolenic acid and derivatives having ω-6 unsaturated fatty acid structures thereof in an amount sufficient for suppressing the hypersecretion of parathyroid hormone of said patients.

2. A method according to claim 3, wherein the amount of said at least one ω-6 unsaturated fatty acid composition administered to said patients is in the range of from 50 mg/day to 600 mg/day per patient.

* * * * *

UNITED STATES PATENT AND TRADEMARK OFFICE
CERTIFICATE OF CORRECTION

PATENT NO. : 5,668,174
DATED : Sept. 16, 1997
INVENTOR(S) : Fumikazu Kawagishi, et al It is certified that error appears in the above-identified patent and that said Letters Patent is hereby corrected as shown below:

On title page, item [73] add the following:
--and Idemitsu Materials Co., Ltd., Tokyo, Japan--

Signed and Sealed this

Seventeenth Day of February, 1998

Attest:

BRUCE LEHMAN

*Attesting Officer*  *Commissioner of Patents and Trademarks*